United States Patent [19]

Pelanne

[11] 3,987,660

[45] Oct. 26, 1976

[54] METHOD OF DETERMINING THERMAL CONDUCTIVITY OF FIBER INSULATION

[75] Inventor: Charles Marcel Pelanne, Littleton, Colo.

[73] Assignee: Johns-Manville Corporation, Denver, Colo.

[22] Filed: Mar. 25, 1974

[21] Appl. No.: 454,528

[52] U.S. Cl. .............................. 73/15 A; 250/559; 250/571; 356/201
[51] Int. Cl.² .................. G01N 25/00; G01N 21/30
[58] Field of Search ........... 250/222, 559, 571, 572, 250/562, 341, 338; 356/201; 73/159, 15 A

[56] References Cited
UNITED STATES PATENTS

| | | |
|---|---|---|
| 2,312,626 | 3/1943 | Chamberlin et al. ............ 250/562 X |
| 3,075,377 | 1/1963 | Lang ................................... 73/15 A |
| 3,496,366 | 2/1970 | Hunziker et al. ............... 250/223 X |
| 3,573,476 | 4/1971 | Falcoff et al. ....................... 250/227 |

*Primary Examiner*—Alfred E. Smith
*Attorney, Agent, or Firm*—Robert M. Krone; Joseph J. Kelly; James W. McClain

[57] ABSTRACT

A method is disclosed for the determination of the thermal conductivity of low density matted inorganic fiber insulating bodies by transmission of visible light through such bodies. The method is particularly applicable to fiber glass bodies. Densities must be such that radiation is the principal heat transfer mechanism.

11 Claims, 3 Drawing Figures

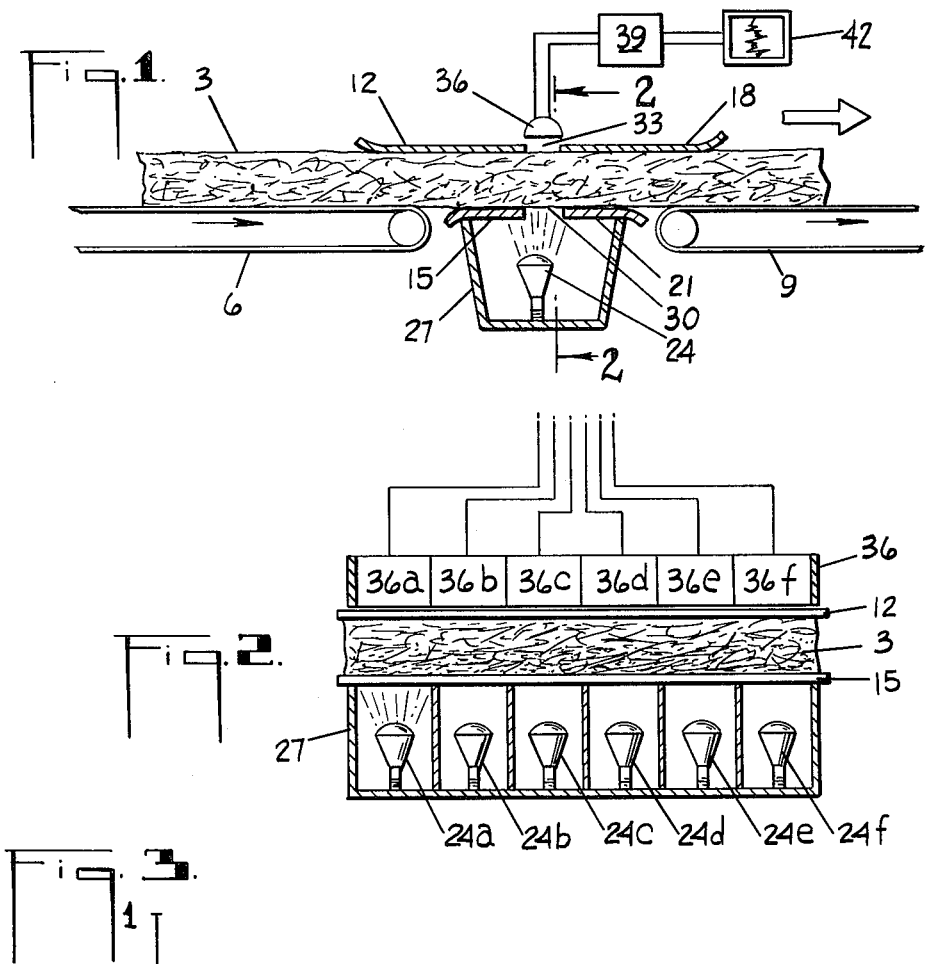
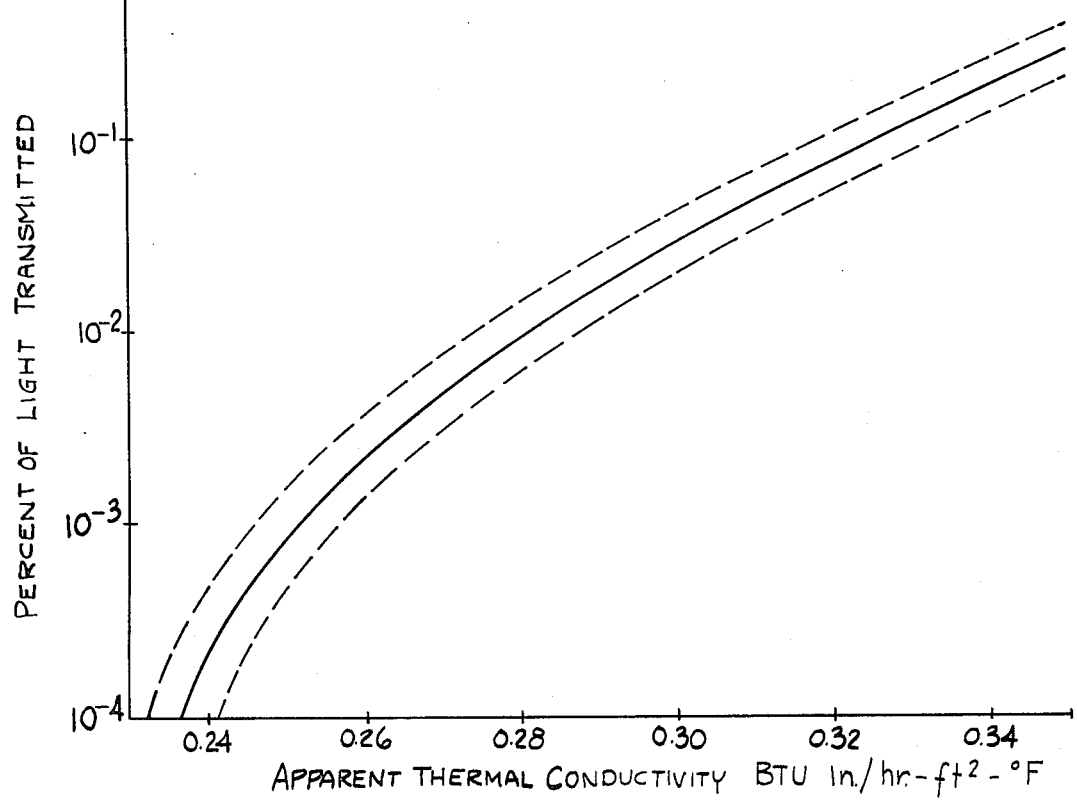

METHOD OF DETERMINING THERMAL CONDUCTIVITY OF FIBER INSULATION

BACKGROUND OF THE INVENTION

1. Field of the Invention

This invention relates to processes for the determination of thermal conductivity (or its converse, thermal resistance) of low density inorganic fiber mats by light transmission.

Inorganic fiber mats, particularly glass fiber mats in various thicknesses, are widely used both in construction and industry for thermal insulation purposes. The structure of such mats consists of fibers (often coated or treated with various materials) felted together in a bulky, low density open mesh network. Within this network are a myriad of minute dead air spaces bound by radiantly absorbing fiber surfaces.

It is these dead air spaces and surfaces that provide the major portion of the insulating property of the fiber mat. Because of this, thermal conductivity through the mat is a direct function of various physical properties of the mat, including the bulk (or "apparent") density, the predominant fiber orientation (if any), and the nominal fiber diameter.

"Apparent thermal conductivity," which is defined as the thermal conductivity of the bulk mat, can be measured by a number of standard methods. Typical of these is the "guarded hot plate" method described in A.S.T.M. Method C-177. All of these standard tests, however, are subject to critical limitations. The first limitation is that most of the thermal conductivity measurement methods are essentially "batch" methods as compared to "continuous" methods. That is, they require that a sample of the mat be removed and tested separately away from the main body of the mat. Beside the obvious inconvenience of such a procedure, these methods destroy the integrity of the mat and can produce misleading results if the sample chosen happens not to be representative of the bulk mat. (This situation occurs quite frequently, for the bulk mat is far from homogeneous. There is some variation of physical properties, including density and thermal conductivity, from region to region throughout the mat. The chances are quite high, therefore, that the small sample removed for testing will not be truly representative of the average properties of the mat.)

These testing methods are also quite time consuming. The sample must be removed from the mat and placed in the testing apparatus. The apparatus must be calibrated, if it is a heat flow type apparatus, and brought to stable operating temperatures. Thereafter, the test must be run for a sufficient length of time to obtain good results. The sample is then removed and the apparatus made ready to receive the next sample. The long period of time required to conduct such a test on a single sample obviously severely limits the number of samples which can be tested and therefore also limits the degree to which the overall properties of the entire glass mat can be accurately determined.

It is therefore an object of this invention to provide a method of determining thermal conductivity of fiber mats which could operated on a continuous basis to analyze the entire bulk mat and which could give values averaged over various areas of the mat. Further, such a process should not physically harm or alter the mat. The process of the present invention is a measurement method combining all these desirable properties.

DESCRIPTION OF THE PRIOR ART

A wide variety of methods of determining thermal conductivity are described in the art. These are almost invariably heat flow methods. In these methods a temperature differential is maintained across the thermal insulation and the heat flow from the hot side to the cool side over a given period of time is measured. Typical of such tests is the aforesaid A.S.T.M. Method C-177. Also representative are processes such as those described in U.S. Pat. Nos. 3,552,185 and 3,075,377.

Light transmission and other optical means have been used in the past for continuous determination of the density and/or thickness of a nonopaque medium. Typical of such processes are those described in U.S. Pat. Nos. 2,361,217 (measurement of yarn thickness); 2,466,615 (measurements of the density of a cotton picker lap); 2,517,330 (measurement of the density of sheets of paper); and 3,157,915 (measurement of the density of felt webs for hat manufacture). Many of these patents also describe means for using the density or thickness measurement obtained by optical means to control feed mechanisms supplying wool, cotton, etc., to the web or mat which is being inspected. By these methods, the optical measurement is used as a means of obtaining a relatively uniform density or thickness of the product mat.

SUMMARY OF THE INVENTION

The invention herein is a method of determining the thermal conductivity of low density matted inorganic fiber bodies, such as thermal insulation, by means of light transmission. The method permits continuous thermal conductivity determinations and can determine the average thermal conductivity over large or small portions of the mat. The method relies for its effectiveness solely upon light; it does not involve heating of any portion of the mat nor any disruption of the physical integrity of the mat.

The invention herein is a process for the determination of the apparent thermal conductivity of a low density matted inorganic fiber insulating body which comprises impinging a beam of visible light on a surface of the body; detecting at a point of the surface of the body substantially opposite to the point of impingement the amount of said visible light transmitted through the body; and thereafter determining the apparent thermal conductivity of the body from the amount of transmitted visible light according to a predetermined correlation. In a preferred embodiment the light beam passes through the body in a line normal to the plane of principal orientation of the fibers.

BRIEF DESCRIPTION OF THE DRAWING

FIG. 1 schematically illustrates the process of this invention.

FIG. 2 illustrates schematically in enlarged detail the use of this process to determine the thermal conductivity of either small areas of the fiber mat or large integrated areas of the mat.

FIG. 3 is a typical correlation curve relating to percentage of light transmitted to the apparent thermal conductivity of one type of glass fiber mat.

DETAILED DESCRIPTION OF THE INVENTION

The invention herein is a method for determining the apparent thermal conductivity of low density matted inorganic fiber bodies by means of light transmission.

By the process of this invention a fiber mat can be continuously inspected and the apparent thermal conductivity of various regions of the whole mat continuously determined as the mat moves through the manufacturing process. If desired, the process of this invention for determining thermal conductivity can also be adapted to control various physical properties of the mat, such as density, in order to obtain a more uniform conductivity throughout the mat.

The method herein relies solely upon light for its effectiveness. It does not require heating the mat. Neither does it require destroying the physical integrity of the mat by cutting one or more sections out of the mat for separate thermal conductivity determinations.

In addition, the process of this invention permits conductivity measurements on large or small areas of the mat. The correlations used are such that even considering the effect of differing physical properties such as density, fiber orientation and/or type of fiber, conductivity values within an acceptable degree of accuracy can be readily obtained. Consequently, the process of this invention has great versatility in that it allows a wide variety of fiber mats to be analyzed for thermal conductivity with satisfactory results without recalibration. Of course, if one recalibrates to account for the varying physical characteristics of the different mats, greater degrees of accuracy can be obtained.

The invention herein is a process for the determination for the apparent thermal conductivity of a low density matted inorganic fiber body, such as a mat of thermal insulation, which comprises impinging a beam of visible light on a surface of the body; detecting at a point of the surface of the body substantially opposite to the point of impingement the amount of the visible light transmitted through the body; and thereafter determining the apparent thermal conductivity from the amount of transmitted visible light according to a predetermined correlation. In a preferred embodiment the light beam passes through the body in a line normal to the plane of principal orientation of the fibers.

The process of this invention may be more readily understood by reference to the drawings. In FIG. 1, a continuous fiber mat 3 is moved in the direction indicated by the large arrow by conveyor belts 6 and 9. This mat is compressed between guide plates 12 and 15 to a specified thickness, normally the nominal commercial thickness at which the mat will be sold. Since there is a variation of thermal conductivity of bulk materials with density, it is customary in the insulation industry to specify the thermal conductivity of a commercial material at a particular thickness. If later handling or usage causes a change in the density, the user then has a point of reference from which he can determine the correct thermal conductivity at the new density. Guide plates 18 and 21 serve to retain the mat at this specified thickness until the mat has passed the thermal conductivity measurement section of the process.

The thermal conductivity measurements are made as the fiber mat passes through the space between the trailing edges of guide plates 12 and 15 and the leading edges of guide plates 18 and 21. In this region, the upper and lower faces of the fiber mat are completely exposed. A light source 24 is enclosed in a container 27 which completely surrounds the light source and presents an opaque barrier on all sides except directly beneath the fiber mat. The light from light source 24 passes through opening 30 and impinges upon the underside of fiber mat 3. The mat absorbs most of the light impinging upon it, but a small portion passes directly through the mat to reach opening 33 on the opposite side of the mat.

The geometry of the light transmission system is such that light sensing means 36, being mounted directly opposite opening 33, senses only light that in effect has traveled across mat 3 in a straight line from the point on the underside of mat 3 which is directly opposite light sensing means 36. The light will, of course, be scattered as it passes through the fiber mat 3, but scattering out of the nominal straight line path will be compensated for by scattering into the path, so in practice the light transmission can be assumed to follow the straight line path. It would be possible, of course, to offset light sensing means 36 so that the straight line from opening 30 is not the shortest path across mat 3. That does not alter the method of this invention, but merely causes additional attenuation of the light. Since such offsetting of either the light source 24 or the light sensing means 36 is within the scope of the invention, and since it does not effect the principle of the invention, it will not be further discussed. Transmission of the light beam through the mat to a sensor "substantially opposite" will mean both placement of sensors directly opposite opening 30 and also offset. Illustration herein will be of directly opposite placement.

In many fiber glass mat production processes, the fibers tend to orient themselves in a plane with their long axes parallel to the upper and lower surface of the mat. In a preferred embodiment of the invention therefore, the light beam from light source 24 reaching opening 33 traverses mat 3 in a direction substantially normal to the plane of principal orientation of the fibers in mat 3.

The light passing through opening 33 is detected by light sensing means 36. Light sensing means 36 also contains means for converting the quantity of light detected to a proportional electrical output signal. This signal is transmitted to detection and analysis apparatus 39. Detection and analysis apparatus 39 in turn converts the signal into visible or otherwise comprehensible output. For instance, in FIG. 1 apparatus 39 runs recorder 42 which in turn produces a time chart with a curve proportional to the instantaneous signal originally generated by light sensing means 36.

The total amount of light transmitted through the fiber body is usually a very small fraction of the total amount emitted by source 24 and impinging on the surface of the mat proximate to source 24, normally being from $10^{-6}$ to 10 percent, usually $10^{-4}$ to 1 percent. The exact amount of light transmitted is not critical, however, as long as it is consistent as related to the total light emitted and the calibration. Conventional light sensing devices are commercially available to accurately sense even the very small transmitted light fractions.

FIG. 2 illustrates in detail one preferred embodiment of this invention. This view, taken on plane 2—2 of FIG. 1, shows a full longitudinal view of the light source and the light sensing means. In this particular embodiment the light source 24 comprises a plurality of individual light bulbs 24a to 24f. Each of these bulbs is of known and essentially constant intensity. In the embodiment shown, each is individually enclosed in a separate compartment open only at the top (i.e., adjacent to opening 30). Each light bulb is separately controllable.

Directly opposite each light bulb is an individual light sensing and converting device such as a photo cell. These are designated 36a to 36f. The light passing from a particular bulb through mat 3 is detected by the light sensing device opposite. The sensing device converts the light detected into a proportional signal which is sent through an individual lead to the detecting and recording devices.

Alternatively, a single line light source providing uniform light density across the mat may be used. Appropriate light sensing means would also be provided for use in conjunction with the single line light source.

The apparatus may be used to operate the process in two principal modes. In the first, illustrated in FIG. 2, individual lights are used either separately or in small groups to measure the thermal conductivity in limited regions of the fiber mat. For instance, in FIG. 2 only light 24a is shown as on and only sensing device 36a would be activated. Consequently, the thermal conductivity measurement would be limited to that outer region of mat 3 lying between light 24a and sensing device 36a. Alternatively, all of the individual lights (or the single line light source) can be used giving a measure of the thermal conductivity across the entire mat. Sensing devices 36a to 36f may have their output signals combined as an indication of the integrated total thermal conductivity across the mat or the signals may be detected and recorded individually (such as by a multiple recording device) so that the variation of thermal conductivity across the entire mat can be determined.

In addition to the use of lights individually, in small groups, or all together, means (not shown) may be provided for altering the width of openings 30 and 36. The larger width openings will provide an average value for the thermal conductivity in a larger portion of the mat adjacent the opening and measured in the direction of travel of the mat. For instance, if the unit length of the mat being measured is only 1 inch (i.e., openings 30 and 33 are restricted to 1 inch in width) localized variation in the thermal conductivity as measured by the light transmitted will be noted. However, if the widths of openings 30 and 33 are expanded to, for instance, 6 inches, the broader unit length of mat being examined will have an inherent integrating and averaging effect so that the localized thermal conductivity variation from one unit length to the next will be somewhat less than with the 1 inch unit length.

The determination of thermal conductivity from the detection of the amount of light transmitted will be obtained from a predetermined correlation which includes the factors of insulation matrix characteristics, degree of error permitted, and the thickness of mat (which is fixed by the spatial separation of guide plates 12 and 15). To determine the correlation, the spacing of guide plates 12 and 15 is first set at a predetermined distance, usually equal to the nominal thickness at which the fiber insulation mat will later be sold. The light detection apparatus is then calibrated, both for the entire array of bulbs and for each individual or separate group of bulbs which it is intended to use. This calibration, made with no mat between plates 12 and 15, is taken as the control or 100% light transmission. (During this calibration, and during the actual thermal conductivity measurements, customary means are taken to shield the apparatus from any significant amount of light from extraneous sources.) Thereafter, various mats of the same fiber and of known thermal conductivity at the stated thickness are inserted seriatim into the apparatus and the amount of light transmission for each with the desired light arrays is determined. The thermal conductivities of the mats are chosen to provide reference points across the entire range of thermal conductivities which it is desired to determine for the test mats. From the data thus derived, the correlation between light transmission and thermal conductivity for the given type of insulation and mat thickness is determined. A typical such correlation is shown in FIG. 3. This is a correlation for mats of 1 inch thickness and composed of glass fibers having a nominal fiber diameter of 4.5 microns. The density of these mats ranged from 0.3 to 1.7 pounds per cubic foot. In a series of measurements on 17 different mats of 1 inch thickness and known thermal conductivity, over 70% of the data points obtained fell within 2% of the solid line (i.e., within the range indicated by the two dotted lines). This correlation held true whether the fibers were oriented predominantly in the direction of travel of the mat or were randomly distributed in the horizontal plane normal to the direction of light transmission.

These predetermined correlations hold true for large numbers of mats of relatively similar properties. Even substantial changes in various physical properties of the mats require only small changed in the correlations, and in fact, reasonably accurate results can be obtained from correlations from relatively dissimilar materials. For instance, a reduction of a nominal glass fiber diameter in the mat by a factor of almost three results in only a seven percent error in the apparent thermal conductivity of the mat containing the finer glass fibers as determined by the correlation in FIG. 3 for the 4.5 micron glass fibers. This may be contrasted with conventional correlations between physical properties such as density in which an equal change in fiber diameter results in differences in thermal conductivity measurements of 25% or greater.

FIG. 3 illustrates graphically a typical correlation between light transmission and thermal conductivity. Such correlations, however, need not be in the form of graphical plots. It would be quite effective, for instance, to program a conventional computer with each of the correlations desired. This computer could be linked to or made part of apparatus 39. By means of a single input to the computer, such as punched cards, tape, or electrical sensors directly connected to plates 12 and 15, to indicate the particular parameters of the mat, the variable features such as thickness could be automatically compensated for by the computer acting upon the signal generated by light sensing means 36. The output data recorded by recorder 42 would therefore be correct in absolute terms for each type of mat being studied.

In addition, if desired, the output signal of light sensors 36 may be adapted through apparatus 39 to operate upstream control devices which determine the amount of fiber being incorporated into the mat. By this means, thermal conductivity of the mats may be to some extent controlled and made uniform. Typical of such control schemes are those illustrated in the aforesaid patents.

The process of this invention is useful in that density range of the fibrous mats in which radiation is the primary mechanism of heat transfer. When the density of the mat becomes such that conduction among the fibers becomes the controlling mechanism of heat transfer, the process described therein no longer operates. Typical curves of thermal conductivity vs. density for loose fibrous insulations, illustrating the separate radiation and conduction regions, are shown by Wilkes, *Heat Insulation* (1950), in FIG. 4–3. Each different type of fibrous insulation will of course have its own particular curve, but all show the two-region characteristic illustrated by Wilkes. For the types of mineral fibers contemplated herein, "apparent density" (i.e., the bulk density of the fibrous mat) will be no more than 2.0 lbs/ft$^3$, preferably no more than 1.6 lbs/ft$^3$. Minimum densities are not critical, but normally are on the order of 0.3 to 0.5 lbs/ft$^3$.

The process of this invention is applicable only to low density mats made of inorganic fibers. Mats made of materials, such as organic fibers, are not believed to possess the same clear-cut correlations between light transmission and thermal conductivity. The inorganic fibers of the mats for this process may be any conventional inorganic fibers, and may be produced by any conventional method. In a preferred embodiment of the invention, the fibers will be glass fibers. A detailed description of glass fibers and their methods of manufacture will be found in Oleesky et al., *Handbook of Reinforced Plastics* (1964); the pertinent portions of this book are herein incorporated by reference. Other fibrous materials may be silica-alumina fibers, rock wool fibers, mineral wool fibers or the like.

What I claim is:

1. A process for the determination of the apparent thermal conductivity of a low density matted inorganic fiber body without significant physical distortion or heating of the body, which commprises impinging a beam of visible light on a surface of the body; detecting at a point on the surface of the body substantially opposite to the point of impingment the amount of said visible light transmitted through said body; and thereafter determining said apparent thermal conductivity from said amount of transmitted visible light according to a predetermined correlation.

2. The process of claim 1 wherein the beam of visible light traverses said matted inorganic fiber body on a line substantially normal to the plane of principal orientation of the fibers in said matted mineral fiber body.

3. The process of claim 1 wherein said thermal conductivity measurement is made continuously.

4. The process of claim 1 wherein the density of said matted inorganic fiber body is not more than 2.0 lbs/ft$^3$.

5. The process of claim 6 wherein said density is not more than 1.6 lbs/ft$^3$.

6. The process of claim 1 wherein said inorganic fiber comprises glass fiber.

7. Apparatus for determining the thermal conductivity of a low density matted inorganic fiber body by means of light transmission and without significant physical distortion or heating of the body, which comprises:
   a. a light source;
   b. light sensing means positioned to detect essentially only that light emitted from said light source which passes through said matted inorganic fiber body;
   c. means for converting the amount of transmitted light sensed by said sensing means into a proportional electrical signal; and
   d. means for converting said proportional electrical signal by a predetermined correlation into a comprehensible output proportional to the thermal conductivity of said matted inorganic fiber body.

8. The apparatus of claim 7 wherein said light sensing means is positioned so as to detect only that light emitted from said light source which traverses said matted inorganic fiber body on a line substantially normal to the plane of principal orientation of the fibers in said matted inorganic fiber body.

9. The apparatus of claim 7 further comprising means for moving said low density matted inorganic fiber body into a position between said light source and said sensing means.

10. The apparatus of claim 7 wherein said light source comprises a plurality of individual lights arranged in an array transversely across the path of motion of said body, and said sensing means comprises a plurality of individual sensors, each positioned on the opposite side of said body from and directly opposite a corresponding individual light.

11. The apparatus of claim 10 wherein said light source comprises a single line light source extending transversely across said matted inorganic fiber body and having a uniform light density throughout its length.

* * * * *